United States Patent [19]

Muetze et al.

[11] Patent Number: 5,053,328
[45] Date of Patent: Oct. 1, 1991

[54] PROCESS FOR THE FERMENTATIVE PREPARATION OF L-AMINO ACIDS FROM ALPHA KETO CARBOXYLIC ACIDS

[75] Inventors: Bernhard Muetze; Christian Wandrey, both of Juelich; Wolfgang Leuchtenberger, Bruchkoebel, all of Fed. Rep. of Germany; Toshihisa Ohshima, Kyoto, Japan

[73] Assignees: Kernforschungsanlage Juelich, Juelich; Degussa AG, Frankfurt am Main, both of Fed. Rep. of Germany

[21] Appl. No.: 908,777

[22] Filed: Sep. 18, 1986

[30] Foreign Application Priority Data

Sep. 18, 1985 [DE] Fed. Rep. of Germany ....... 3533198

[51] Int. Cl.$^5$ ............................................. C12P 13/06
[52] U.S. Cl. .................................... 435/106; 435/108; 435/115; 435/116; 435/193; 435/832; 435/833; 435/834; 435/835; 435/836; 435/837; 435/838; 435/839
[58] Field of Search ............... 435/193, 232, 106, 116, 435/108, 115, 833–839

[56] References Cited

U.S. PATENT DOCUMENTS

4,119,493 10/1978 Isowa et al. ........................ 435/832

FOREIGN PATENT DOCUMENTS

0101653 8/1983 European Pat. Off. .
0140503 8/1984 European Pat. Off. .
3427495 2/1985 Fed. Rep. of Germany .
59-34890 2/1984 Japan .

OTHER PUBLICATIONS

Chemical Abstract, 100:13728w, "Reaction Technology of the Enzymically Catalyzed Production of L-Alanine", (1983), Fiolitakis et al.
Chemical Abstract; 98:51907g, "Multienzyme Systems in Membrane Reactors", (1982), Wandrey et al.
Chemical Abstract, 85:174086c, "Regulatory Control and Function of Alanine Dehydrogenase from a Thermophilic Bacillus", Epstein (1976).
R. E. Buchanan et al., "Bergey's Manual of Determinative Bacteriology", (1975).
K. Yamada et al., "The Microbial Production of Amino Acids", (1972).
Chemical Abstracts, 104:65540m, "Screening of Thermostable Leucine and Alanine Dehydrogenases in Thermophillic Bacillus Strains", (1985).
Matsumoto et al., "Studies on DL-Alanine Formation by Thermophilic Bacteria", Agr. Biol. Chem., vol. 31, No. 12, pp. 1381–1388, 1967.

*Primary Examiner*—Robert J. Warden
*Assistant Examiner*—Timothy M. McMahon
*Attorney, Agent, or Firm*—Foley & Lardner

[57] ABSTRACT

The preparation of an L-amino acid, particularly valine, leucine, isoleucine, alanine and phenylalanine, from the corresponding α-keto carboxylic acid by bacterial fermentation in the presence of ammonium ions is carried out with the aid of thermophilic Bacillus strains at temperatures above 45° C., in particular above 60° C. Bacillus strains DSM 406, 452, 461, 42, 463, 465 and 466 are particularly suitable for this purpose. The greater solubility of the amino acid at the elevated fermentation temperature permits the separation out of the amino acid from the reaction mixture simply by cooling, whereafter the depleted reaction mixture can be pumped back into the fermenter. Especially favorable yields are achieved by supplying oxygen to the fermenter to an amount of less than about 20% dissolved oxygen.

15 Claims, 1 Drawing Sheet

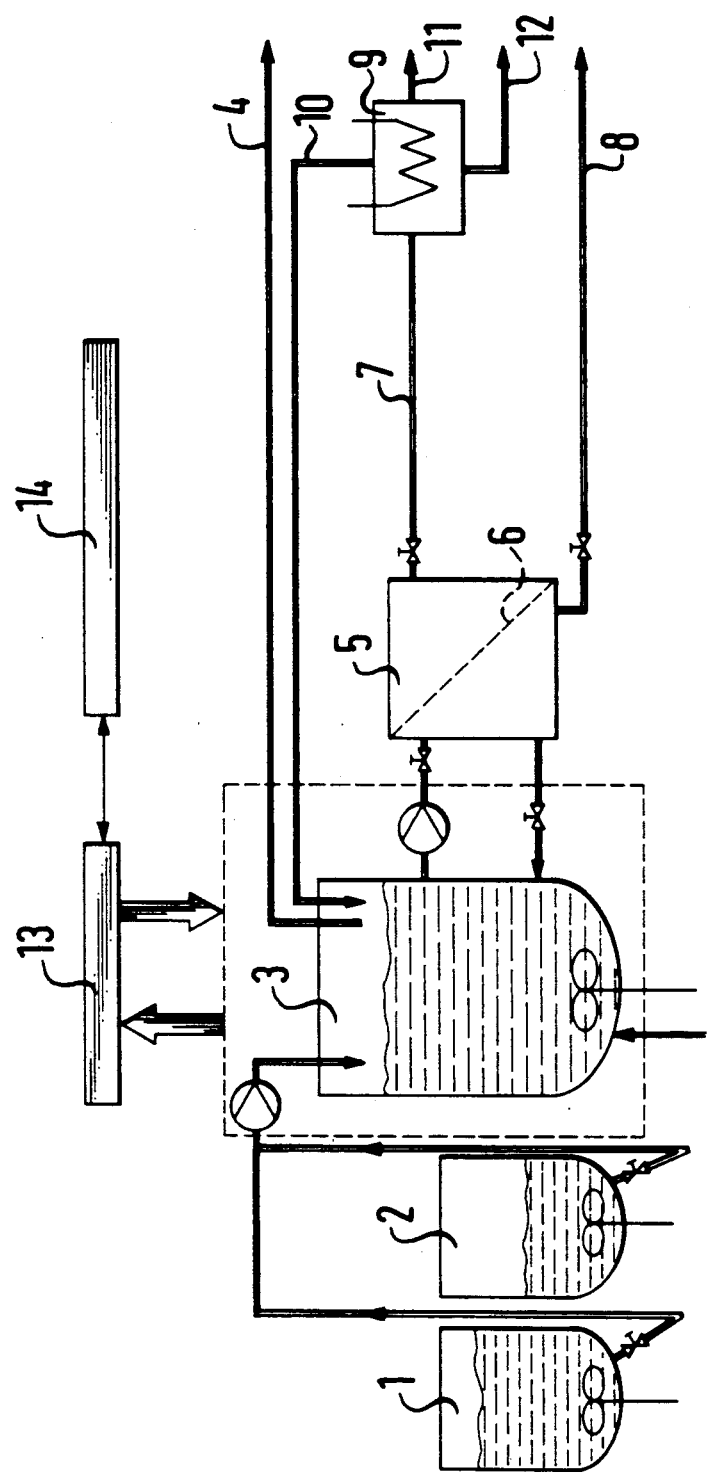

PROCESS FOR THE FERMENTATIVE PREPARATION OF L-AMINO ACIDS FROM ALPHA KETO CARBOXYLIC ACIDS

BACKGROUND OF THE INVENTION

The present invention relates to a process for the preparation of L-amino acids from corresponding α-keto carboxylic acids by bacteria fermentation in the presence of ammonium ions.

It is known, for example, from German Offenlegungsschrift No. 3,427,495, that L-amino acids can be prepared from the corresponding keto carboxylic acids by the action of bacteria that excrete glutamic acid, especially bacteria of the genera *Brevibacterium* and *Corynebacterium*, and by the action of *Escherichia coli*. This disclosed conversion entails, in particular, utilization of the logarithmic phase of growth of the microorganisms which mediate the transformation; in this way, conversion of the keto acid form is achieved with up to 100% efficiency at temperatures in the region of 30°–37° C., α-keto carboxylic acid concentrations in the culture broth of about 20–50 g/l, and fermentation times of between 20 and 72 hours.

In a fermentation process of this type, care must be taken to exclude foreign microbes which may compete with the cultured microorganism for nutrients, may utilize the desired product, or may cause other biological interference. The exclusion of microbial contamination from the fermentation environment necessitates special precautions.

SUMMARY OF THE INVENTION

It is therefore an object of the present invention to provide a fermentation process whereby the keto acid-to-amino acid transformation is accomplished with a high yield but without the need for special precautions against microbial contamination.

It is also an object of the present invention to provide a fermentative method for producing L-amino acids wherein the viscosity of the fermentation liquid is reduced and the solubility of the end product enhanced, thereby favoring processing and isolation of the product.

In accomplishing these objects, there has been provided, in accordance with one aspect of the present invention, a process for producing an L-amino acid which comprises the steps of (A) effecting the bacterial fermentation of an α-keto carboxylic acid corresponding to the L-amino acid by a thermophilic *Bacillus* strain in a fermenter, the fermentation occurring in the presence of ammonium ion and at a temperature above 45° C., such that the L-amino acid is produced; and then (B) separating the L-amino acid from the fermentation liquid. In a preferred embodiment, the fermentation process of the present invention is carried out with a fermentation liquid containing less than 20% dissolved oxygen.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The drawing schematically depicts a device that is suitable for implementing the above-described process of the present invention.

DETAILED DESCRIPTION OF THE PREFERRED EMBODIMENTS

It has now been found that the risk of foreign microbes can be reduced and, moreover, high space/time yields and additional process advantages can be achieved when the microbiological conversion of α-keto carboxylic acids into the corresponding L-amino acids is carried out at elevated temperatures with the aid of thermophilic *Bacillus* strains. Since the process of the present invention is carried out at a temperature above 45° C., and preferably above 60° C., biological interference by common microbial contaminants is substantially reduced or eliminated.

In addition to reducing the risk of contamination by foreign microbes in the fermentation environment, the reductive amination of α-keto acids at elevated temperatures, according to the present invention, provides the advantage of decreasing the viscosity of the fermenter contents. The present invention thereby makes possible higher filtration throughputs in the retention of biomass and lower energy costs for agitation and pumping of the fermentation liquid. Furthermore, there is an increase in the solubility limit of the amino acids formed, so that higher product concentrations in solution can be attained, which in turn facilitates isolation of the L-amino acid end products.

It has been known for some time that certain amino acids could be obtained using thermophilic bacteria at elevated temperature, for example, in the formation of DL-alanine from glucose at 50°–65° C. by the action of *Bacillus coagulans* $B_g$-17 (see *Agr. Biol. Chem.* 31: 1381–88 (1967). But the specific utility and benefits of converting an α-keto carboxylic acid to the corresponding L-amino acid at elevated temperature with the aid of thermophilic bacteria have not been recognized heretofore. The process according to the present invention can be used, in particular, for the formation of valine from o-ketoisovalerate, leucine from α-ketoisocaproate, isoleucine from α-keto-β-methylvalerate, alanine from pyruvate, and phenylalanine from phenylpyruvate.

Examples of thermophilic Bacilli that are suitable for use in the present invention are:

| | |
|---|---|
| *Bacillus caldothenax* | DSM 406 |
| *Bacillus* spec. | DSM 411 |
| | DSM 405 |
| | DSM 465 |
| | DSM 466 |
| | DSM 1519 |
| | DSM 1520 |
| | DSM 1521 |
| | DSM 730 |
| *Bacillus sphaericus* | DSM 461 |
| | DSM 462 |
| | DSM 463 |
| *Bacillus stearothermophilus* | DSM 458 |
| | DSM 1550 |
| *Bacillus coagulans* | DSM 460 |
| | DSM 2320 |
| and | |
| *Bacillus acidocaldarius* | DSM 452, | where the acronym "DSM" denotes the accession number assigned a culture deposited at the Deutsche Sammlung von Mikroorganismen in Gottingen, Federal Republic of Germany.

The foregoing strains are particularly suitable for the formation of leucine and alanine pursuant to the present invention. The strains *Bacillus acidocaldarius* DSM 452, *Bacillus* sp. DSM 465 and DSM 466, *Bacillus sphaericus* DSM 461, 462 and 463, and *Bacillus caldothenax* DSM 406 have also proven particularly useful for the transformation of α-keto-isocaproate into L-leucine and pyruvate to alanine. In any event, a wide variety of bacterial strains from the group of thermophilic Bacilli can be used in the present invention.

Low-cost carbon compounds like acetate and glycerol can be used as cosubstrates in the present invention to provide an additional energy source for the fermenting microorganisms. The acetate which is consumed during fermentation can be easily replaced by pH-controlled metering of acetic acid into the nutrient medium. The glycolysis route can be bypassed by the use of acetate.

Fermentation in accordance with the present invention can be carried out in a batch process or continuously. The retention of biomass during continuous fermentation, using filter systems or by centrifugation, results in the discharge from the fermenter of essentially exhausted medium along with the product, while some or all of the microorganisms can be returned to the fermenter. It is particularly advantageous to operate in a continuous-flow reactor. The amino acid is obtained from the culture filtrate by cooling in a crystallizer, and the mother liquor is wholly or partially returned to the reactor.

Transformation of the α-keto carboxylic acid into the corresponding L-amino acid, which is favorably rapid at an elevated temperature, results in a fermenter discharge having a low keto acid concentration and a high amino acid concentration. As a consequence, the separating out and obtaining of the amino acid is readily achieved by appropriate cooling (for example, down to a temperature as low as 2° C).

It has also been discovered, surprisingly, that restriction of the $O_2$ supply to the fermenter, particularly to a value that is less than 20% dissolved $O_2$, results in an increase in the product yield achieved with the present invention. For example, in the transformation of α-keto-isocaproate into L-leucine with the aid of *Bacillus caldothenax* at 60° C. and Na isocaproate concentrations of 7.7 g/l, a reduction in the aeration rate from 1 V/V.min to 0.05 V/V.min resulted in an increase in the yield from 50% to 80%.

As shown in the drawing, the process of the present invention can be implemented in fermentation apparatus wherein the substrate is metered from substrate-sterilization vessels 1 and 2 into an aerated fermenter 3, from which the exit air escapes via 4. The aerated and stirred fermenter broth is continuously passed to a separator 5, which has a filter system 6 to retain biomass. The product solution from which biomass has been removed is discharged via 7, while product solution-containing biomass is drawn off via 8. The product solution drawn off from the separator 5 via 7 is transferred to crystallizer 9. Part of the mother liquor is returned via 10 into the fermenter 3. A mother-liquor bleed stream is discharged via 11. Product is discharged at 12. The operation of the fermenter 3 is controlled by a control system 13 with a process computer 14.

The present invention is further illustrated in detail by reference to the following examples:

EXAMPLE 1 L-leucine obtained from α-ketoisocaproate and ammonium using *Bacillus caldothenax* (DSM 406) in a batch fermentation.

The following medium was used for the fermentation: 1 g peptone; 0.5 g yeast extract; 0.5 g meat extract; 6 g Na acetate; 2 g $K_2HPO_4$; 2 g $KH_2PO_4$; 0.1 g Mg $SO_4$; 10.65 g $NH_4CL$; 7.67 g α-ketoisocaproate; and the remainder, to 1 liter, of deionized water (pH 7.2). The medium thus formulated was autoclaved at 120° C. for 20 minutes.

The fermenter which was used had a volume of 3 liters, and the temperature of fermentation was 60° C. The pH was controlled at 7.2 by metering in 100% strength acetic acid, and the acetate consumed during fermentation was replaced in this way. The stirring rate was 800 r.p.m. The fermenter was inoculated with a dense suspension of *Bacillus caldothenax*, which had been cultured on a meat extract/yeast extract/peptone medium. To prevent substrate inhibition, keto acid and ammonium salt were successively replenished. A L-leucine concentration of 17 g/l was achieved in the course of the fermentation. At a high aeration rate of 1 V/V.min, 50% of the keto acid which was consumed was transformed into L-leucine, whereas the corresponding value was 80% at 0.05 V/V.min.

EXAMPLE 2

L-leucine obtained from α-ketoisocaproate and ammonium using *Bacillus caldothenax* in a continuous fermentation with retention of biomass and continuous harvesting of product.

The medium of Example 1 was used for this fermentation. The fermenter volume, as before, was 3 liters. Keto acid and ammonium salt were continuously and separately supplied. The acetate consumed during fermentation was replaced by acetic acid, which was metered in under pH control. The pH was 7.2, the temperature was 60° C., and the inoculation was as in Example 1. The initial air supply was adjusted to 1 V/V.min, in order to reach a high cell concentration by rapid growth. The air was reduced thereafter to 0.05 V/V.min in order to increase L-leucine production, as in Example 1.

Biomass was retained from the fermenter discharge by a filter system and was pumped back into the fermenter. The filtrate was cooled in a crystallizer to separate out the amino acid, and a portion of the mother liquor was returned to the fermenter. The remainder was drained away to be continuously replaced by new medium. L-leucine was crystallized by the cooling, and was pumped away continuously or discontinuously.

The high fermentation temperature of 60° C. resulted in an increase in the saturation concentration of L-leucine, making it possible to keep more product in solution in the fermenter. Hence, more L-leucine could be separated out, by cooling down, than could have been isolated from the fermenter broth of a fermentation conducted at low temperatures. The lower viscosity of the fermenter content at 60° C. increased the filtration throughout and reduced the energy expended for filtration.

The holdup time ($\tau$) was 25 hours in this test. 2.5 g of L-leucine were formed per day and per liter of fermenter content, and 75% of the keto acid which was consumed was transformed into L-leucine. The filter area of the cross-flow microfilter, as supplied by Enka, was 0.036 $m^2$. To prevent the formation of a covering layer, the rate of flow parallel to the filter surface was set at 1 m/s. It was also possible, by nutrient limitation and by the returning of all the cells to the fermenter, to produce L-leucine continuously using stationary cells.

EXAMPLE 3. L-alanine obtained from pyruvate using the thermophilic *Bacillus* species DSM 465 and 466.

The medium of Example 1, with 8 g/l of Na salt of pyruvic acid substituted for α-ketoisocaproate, was used in the fermenter. In addition, glycerol was used in place of acetate. The fermentation conditions were otherwise those of Example 1.

At a dissolved oxygen content of 10% and a temperature of 60° C., 80% of the pyruvate initially introduced into the fermenter was transformed into L-alanine. 5.3 g of L-alanine/l per day were produced.

What is claimed is:

1. A process for producing an L-amino acid selected from the group consisting of L-valine, L-leucine, L-alanine and L-phenylalanine, which comprises the steps of:
   (A) effecting bacterial fermentation of an α-keto carboxylic acid which corresponds to said L-amino acid by a thermophilic *Bacillus* strain in a fermenter, said fermentation occurring in the presence of ammonium ion and at a temperature above 45° C., such that a fermentation liquid containing said L-amino acid is produced; and then
   (B) separating said L-amino acid from said fermentation liquid.

2. A process as claimed in claim 1, wherein said fermentation is carried out at a temperature above 60° C.

3. The process as claimed in claim 1, wherein said fermentation is carried out at a temperature of 60° C. or higher.

4. A process as claimed in claim 1, wherein L-leucine or L-alanine is prepared from α-keto-isocaproate or pyruvate, respectively.

5. The process as claimed in claim 1, wherein at least one compound from the group consisting of acetate, glycerol and glucose are used as cosubstrates for said fermentation.

6. A process as claimed in claim 1, wherein step (B) comprises continuously removing said fermentation liquid from said fermenter, cooling said fermentation liquid to a temperature such that L-amino acid separates out therefrom, and then pumping said fermentation liquor back into said fermenter.

7. The process as claimed in claim 6, wherein in step (A), said fermentation is carried out at a temperature of 60° C. or higher.

8. A process as claimed in claim 1, wherein step (B) comprises retaining in said fermenter biomass comprised of said strain, cooling said fermentation liquid too a temperature such that said L-amino acid separates out therefrom, and then pumping said fermentation liquor back into said fermenter.

9. The process as claimed in claim 8, wherein in step (A), said fermentation is carried out at a temperature of 60° C. or higher.

10. The process as claimed in claim 1, wherein said fermentation liquid in said fermenter contains less than about 20 vol.% dissolved $O_2$ based on total volume of solution.

11. The process as claimed in claim 10, wherein said dissolved oxygen content is about 10%.

12. The process as claimed in claim 10, wherein said *Bacillus* strain is *Bacillus caldothenax*.

13. The process as claimed in claim 12, wherein L-leucine is prepared from α-keto-isocaproate.

14. The process as claimed in claim 13, wherein the reaction temperature is 60° C. or higher.

15. The process as claimed in claim 10, wherein said fermentation is carried out at a temperature of 60° C. or higher.

* * * * *